(12) United States Patent
Svatos

(10) Patent No.: US 6,937,693 B2
(45) Date of Patent: Aug. 30, 2005

(54) OPTIMAL CONFIGURATION OF PHOTON AND ELECTRON MULTILEAF COLLIMATORS IN MIXED BEAM RADIOTHERAPY

(75) Inventor: Michelle Marie Svatos, Oakland, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 170 days.

(21) Appl. No.: 10/387,760

(22) Filed: Mar. 12, 2003

(65) Prior Publication Data

US 2004/0179648 A1 Sep. 16, 2004

(51) Int. Cl.[7] ............................................. A61N 5/00
(52) U.S. Cl. ........................................ 378/65; 378/108
(58) Field of Search ............................ 378/64, 65, 97, 378/108, 147–153, 113, 145; 250/492.1, 505.1

(56) References Cited

U.S. PATENT DOCUMENTS 5,332,908 A * 7/1994 Weidlich ................. 250/492.1
5,870,697 A * 2/1999 Chandler et al. ........... 702/179
6,730,924 B1 * 5/2004 Pastyr et al. ............. 250/505.1

OTHER PUBLICATIONS

Multileaf Collimation of Electrons–Clinical Effects on Electron Energy Modulation and Mixed Beam Therapy Depending on Treatment Head Design, Michael Blomquist, Magnus G. Karlsson, Björn Zackrisson and Mikael Karlsson, Institute of Physics Publishing, Physics in Medicine and Biology 47 (2002) 1013–1024, 12 pages total.

* cited by examiner

Primary Examiner—Edward J. Glick
Assistant Examiner—Hoon Song

(57) ABSTRACT

A radiation therapy method that includes directing a beam along a beam path toward a treatment area. Performing a correction process on the beam, the process includes selectively collimating the beam based on a dose that takes into account bremsstrahlung interactions caused by the beam.

30 Claims, 5 Drawing Sheets

OPTIMAL CONFIGURATION OF PHOTON AND ELECTRON MULTILEAF COLLIMATORS IN MIXED BEAM RADIOTHERAPY

BACKGROUND OF THE INVENTION

1. Field of the Invention

The present invention relates generally to radiation therapy devices, and more particularly, to a removable electron multileaf collimator for use in a radiation therapy device.

2. Discussion of Related Art

Conventional radiation therapy typically involves directing a radiation beam at a tumor in a patient to deliver a predetermined dose of therapeutic radiation to the tumor according to an established treatment plan. This is typically accomplished using a radiation therapy device such as the device described in U.S. Pat. No. 5,668,847 issued Sep. 16, 1997 to Hernandez, the contents of which are incorporated herein for all purposes.

The radiotherapy treatment of tumors involves three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Cure rates for many tumors are a sensitive function of the dose they receive. Therefore, it is important to closely match the radiation beam's shape and effects with the shape and volume of the tumor being treated.

Either primary photon or primary electron beams may be used in radiation therapy. Currently, clinical practice requires substantial manual intervention to use conformal electron treatment. Conformal photon fields typically are shaped using one or more collimating devices positioned between the source and the treatment area. Many of these photon beam collimating devices (multi-leaf collimators or MLCs) are positioned automatically to deliver a desired photon field shape to a treatment area on a patient. Little manual intervention is required to administer photon radiation therapy. A new type of therapy is also emerging, which involves using both photon beams and electron beams in the same treatment, here called "Mixed Beam Radiotherapy". To be practical, Mixed Beam Radiotherapy requires advances in electron delivery, such as an automatic collimating device designed explicitly to shape electrons such as disclosed in U.S. patent application Ser. No. 09/909,513, filed on Jul. 20, 2001, the entire contents of which are incorporated herein by reference. The photon MLC and the new electron MLC need to be coordinated in an optimal way.

FIG. 1 schematically shows a radiation therapy machine 10 that includes a gantry 12 which can be swiveled around a horizontal axis of rotation 14 in the course of a therapeutic treatment. A treatment head 16 is fastened to a projection of the gantry 12. A linear accelerator (not shown) is located inside gantry 12 to generate the high energy radiation required for the therapy. The axis of the radiation bundle emitted from the linear accelerator and the gantry 12 is designated by beam path 18. Electron, photon or any other detectable radiation can be used for the therapy.

During a course of treatment, the radiation beam is trained on treatment zone 20 of an object 22, for example, a patient who is to be treated and whose tumor lies at the isocenter of the gantry rotation. Several beam shaping devices are used to shape radiation beams directed toward the treatment zone 20. For example, a multileaf photon collimator and a multileaf electron collimator can be arranged to shape the radiation beams. Each of these collimators may be separately controlled and positioned to shape beams directed at treatment zone 20.

For example, when the electron beam source is used, the multileaf photon collimator may be fully retracted and the multileaf electron collimator is designed specifically to stop the primary electrons. However, a few electrons in the beam have bremsstrahlung radiation interactions with high atomic number materials in the head of the accelerator that result in a low percentage photon component (3–5%) to the beam that are not stopped by the electron collimator. This component may be considered "leakage" since it may not be noticeably attenuated by the multileaf electron collimator and will cause an unmodulated background component to the distribution. This is not a significant problem for single electron fields, in fact it may be considered useful since it is possible to get an image of the field from this component with an extremely sensitive portal imaging system such as described in U.S. patent application Ser. No. 09/910,526, the entire contents of which are incorporated herein by reference. If electron modulation is introduced, however, the number of segments or individual fields in an Intensity Modulated Radiation Therapy (IMRT) sequence is increased. A significant increase to the integral dose may result if many segments are used because the photon leakage through the multileaf electron collimator is summed from each segment.

One possible solution is to make the leaves of the multileaf electron collimator thick enough to attenuate the photon component, but this increases the size and weight of the accessory considerably. A second possible solution is to use the multileaf photon collimator in such a way that it acts as a "back up" attenuator. This technique will nearly eliminate the photon component outside the field, but the effect of the multileaf photon collimator 116a and jaws 116b on the electron field itself must be considered.

Some of the electrons that contribute to the field at the patient plane originate from scattering off of secondary "sources" along the beamline, such as the scattering foils and the air column just outside of the beam. Thus, the multileaf photon collimator and the jaws block part of the field if they are fitted to the same size and shape as the field defined by the multileaf electron collimator alone. The result is a broadened penumbra and reduced output due to the scattered electrons.

Accordingly, when bremsstrahlung leakage is generated through a multileaf electron collimator, it is desirable to reduce dosage applied to a patient while providing as clean a beam as possible for the mixed beam treatment. The ideal margin for the photon multileaf collimator for each electron field is a compromise between these two competing interests. In general the margin is a function of the secondary electron energy of the secondary electrons generated from the scattered primary electrons.

SUMMARY OF THE INVENTION

One aspect of the present invention regards a radiation therapy device that includes a radiation source that directs a beam along a beam path toward a treatment area and a beam shaping device controllable to selectively collimate the beam. A treatment planning system is connected to the beam shaping device for simulating a beam shape delivered to a treatment zone. The treatment planning system includes a memory that stores treatment data and a correction device that receives the data from the memory and calculates a proper dose that takes into account bremsstrahlung interactions when the beam is present. The correction device controls the beam shaping device based on the calculated proper dose.

A second aspect of the present invention regards a radiation therapy method that includes directing a beam along a beam path toward a treatment area. A correcting process on the beam includes selectively collimating the beam based on a dose that takes into account bremsstrahlung interactions caused by the beam.

Each aspect of the present invention provides the advantage of reducing dosage applied to a patient in the case when bremsstrahlung leakage is generated through a multileaf electron collimator.

Each aspect of the present invention provides the advantage of maintaining a beam with small penumbra and a constant and high output factor. Further characteristics and advantages of the present invention ensue from the following description of exemplary embodiments by the drawings.

DETAILED DESCRIPTION OF THE PREFERRED EMBODIMENTS

Figure 1:
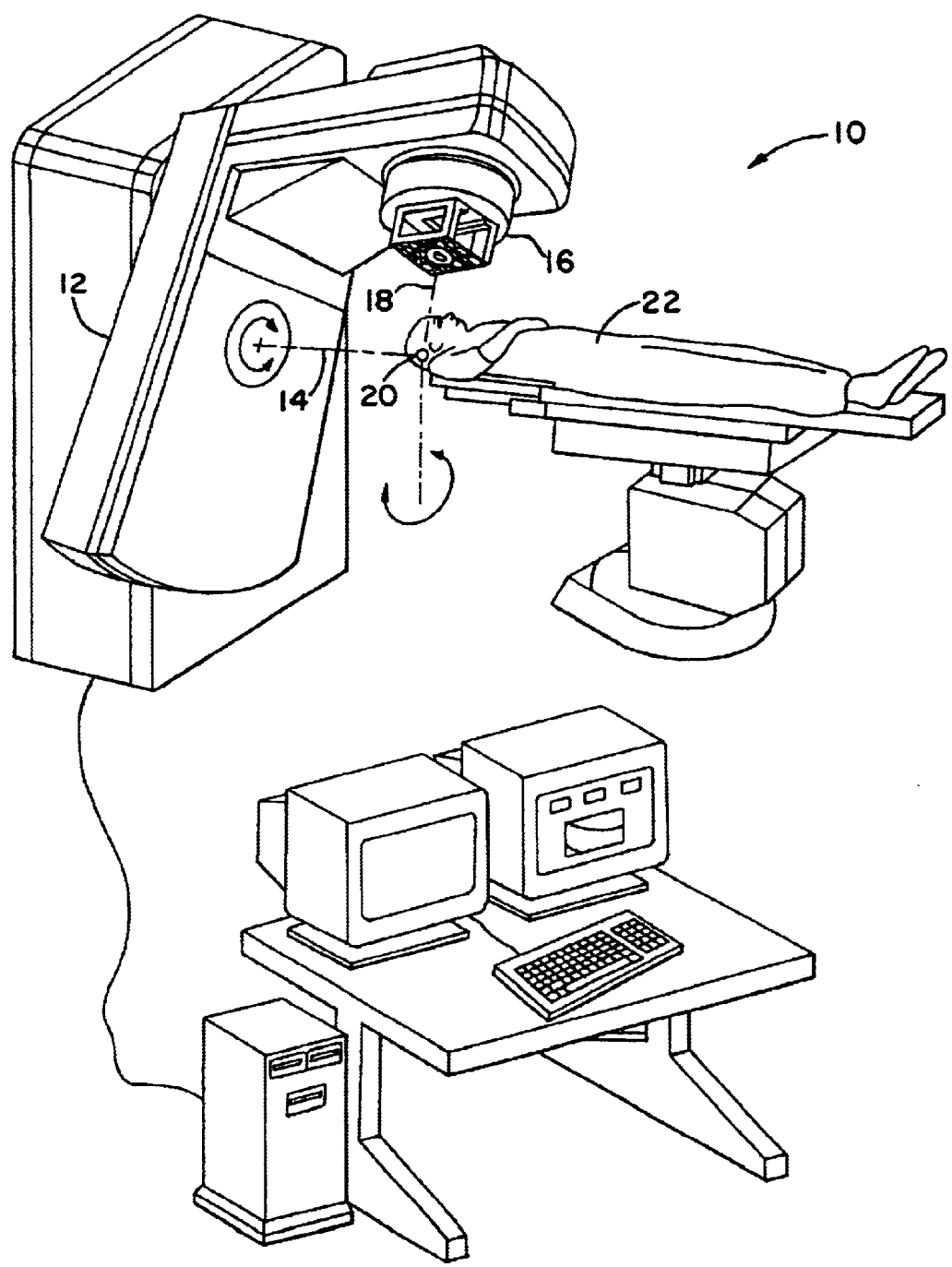
FIG. 1 shows an embodiment of a radiation therapy machine.
Figure 2:
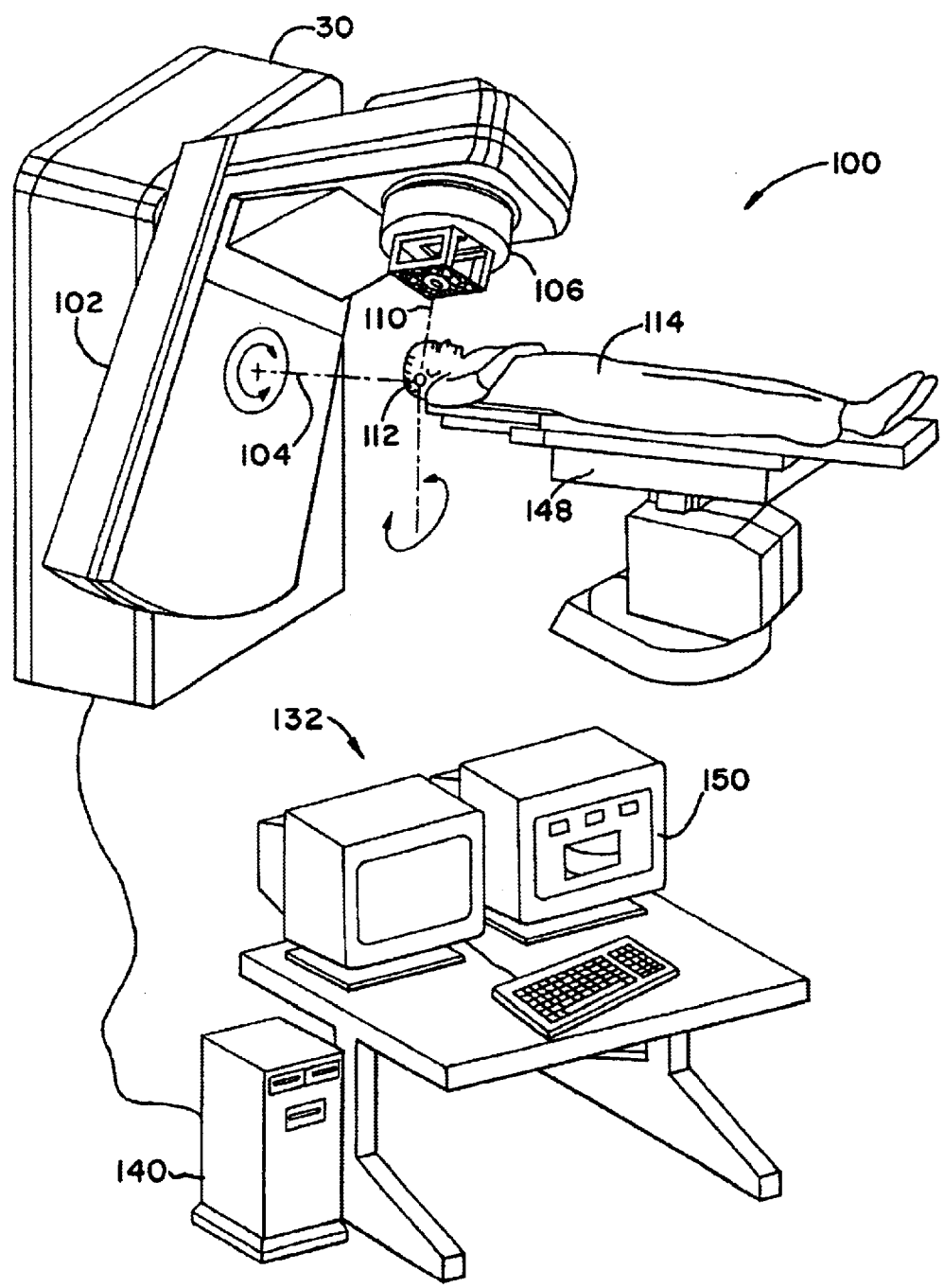
FIG. 2 shows an embodiment of a radiation therapy machine in accordance with the present invention.
Figure 3:
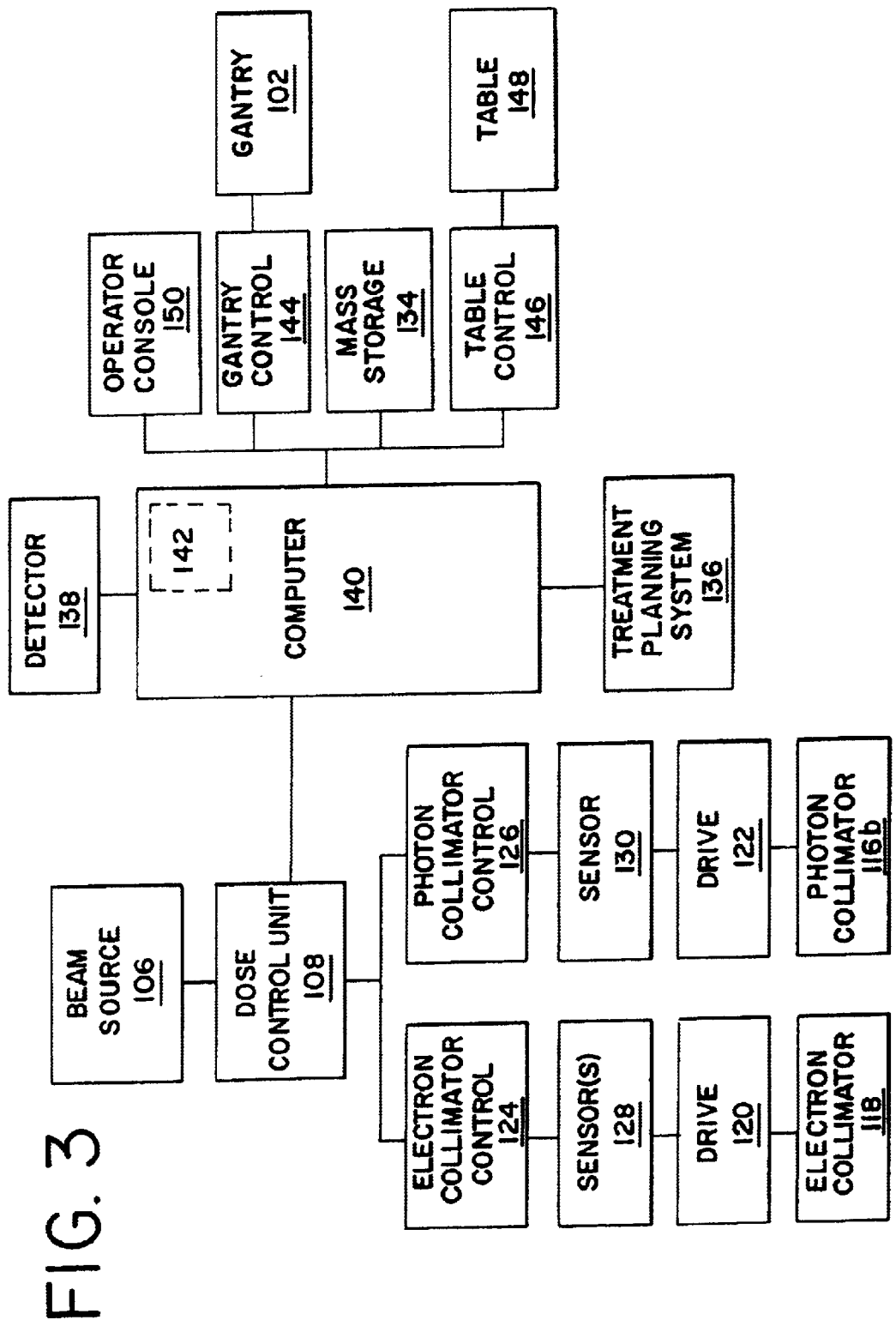
FIG. 3 shows a block diagram illustrating portions of the radiation therapy machine of FIG. 2.
Figure 5:
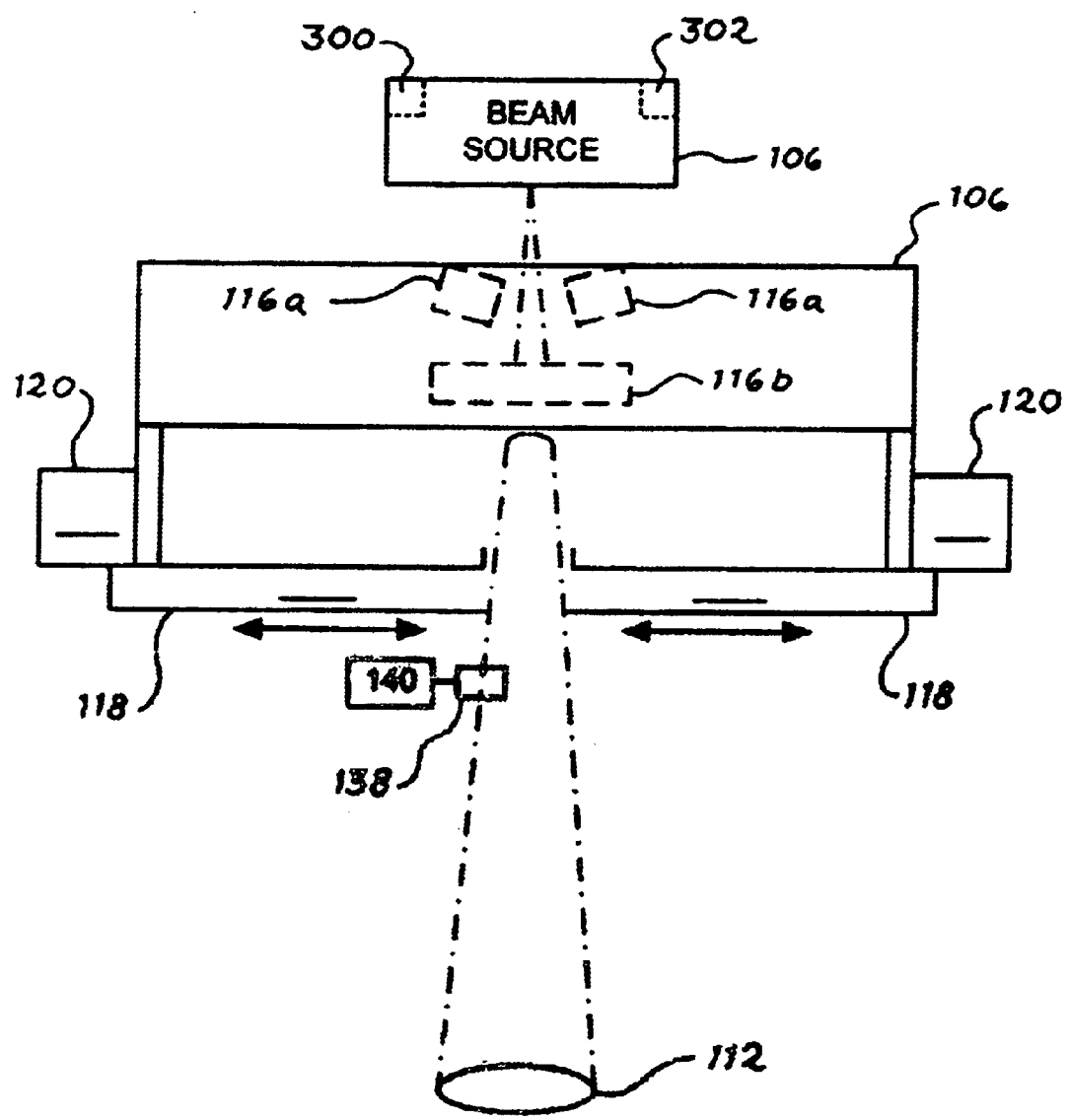
FIG. 5 schematically shows a collimator system to be used with the radiation therapy machine of FIG. 2 in order to execute the method of FIG. 4 in accordance with the present invention.

A radiation therapy machine 100 that incorporates a number of the elements of the radiation therapy machine 10 of FIG. 1 is shown in FIGS. 2 and 3. The radiation therapy machine 100 includes a gantry 102 which can be swiveled around a horizontal axis of rotation 104 during the course of a therapeutic treatment. A beam source 106 is used to generate radiation beams in any of a number of ways well-known to those skilled in the art. For example, the beam source 106 may include a dose control unit 108 used to control a trigger system generating injector trigger signals fed to an electron gun in a linear accelerator (not shown) located inside the gantry 102 to produce the high energy radiation, such as an electron beam or photon beam, required for the therapy. The beam source 106 may include separate sources of radiation 300 and 302 for photons and electrons, respectively, as schematically shown in FIG. 5. The axis of the radiation bundle emitted from the linear accelerator and the gantry 102 is designated by beam path 110.

During a course of treatment, the radiation beam is trained on treatment zone 112 of an object 114, for example, a patient who is to be treated and whose tumor lies at the isocenter of the gantry rotation. Several beam shaping devices are used to shape radiation beams directed toward the treatment zone 112. In particular, a set of photon jaws 116a multileaf photon collimator 116b and a multileaf electron collimator 118 are provided. Each of these collimators, as will be described further below, may be separately controlled and positioned to shape beams directed at the treatment zone 112.

The plates or leaves of the collimators 116b and 118 are made of a material, such as brass, tungsten or lead, substantially impervious to the emitted radiation. The collimator leaves or plates are mounted between the radiation source and the patient and positioned in order to delimit (conform) the field. Areas of the body, for example, healthy tissue, are therefore subject to as little radiation as possible and preferably to none at all.

Note that the plates or leaves of the collimators 116b and 118 are movable such that the distribution of radiation over the field need not be uniform (one region can be given a higher dose than another). In particular, the leaves of each collimator are individually driven by a drive unit 120, 122 and are positioned under the control of electron collimator control 124, photon collimator control 126 and sensor(s) 128 and 130. Drive units 120, 122 move the leaves of each collimator in and out of the treatment field to create a desired field shape for each type of beam. In one embodiment, where an electron beam is to be generated and primary electrons are to be used in a treatment, photon collimator control 126 operates to retract individual leaves of photon collimator 116b, while electron collimator control 124 operates to position individual leaves of electron collimator 118 across the path of the electron beam to generate a desired electron field shape at the isocenter.

Radiation therapy machine 100 also includes a central treatment processing or control unit 132 that is operated by a user. A mass storage device 134 stores data used and generated during the operation of the radiation therapy machine device including, for example, treatment data as defined by an oncologist for a particular patient. This treatment data is generated, for example, using a treatment planning system 136 which may include manual and computerized inputs to determine a beam shape prior to treatment of a patient. Treatment planning system 136 is typically used to define and simulate a beam shape required to deliver an appropriate therapeutic dose of radiation to treatment zone 112.

Figure 4:
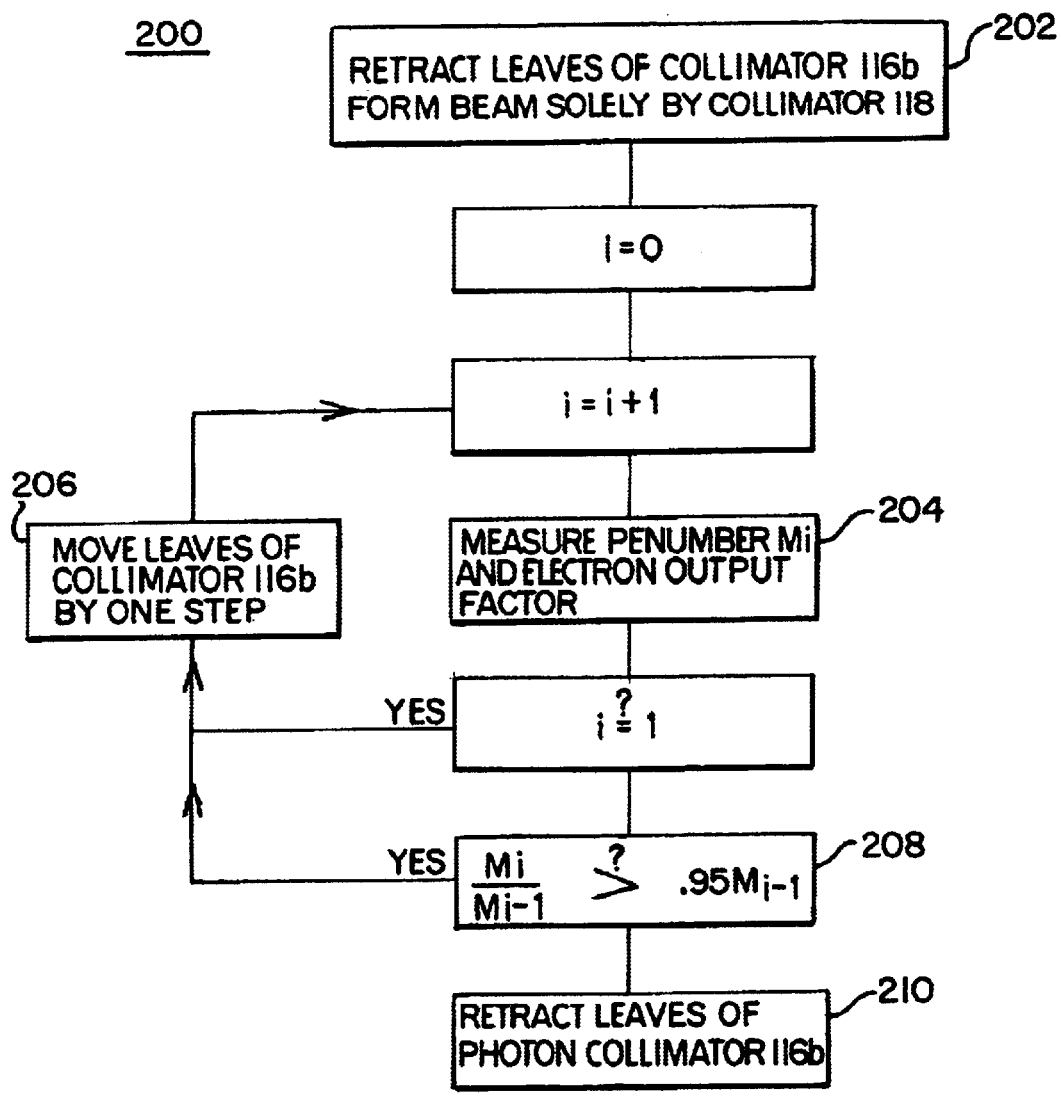
FIG. 4 shows a flow chart that shows a mode of a correction process for the radiation therapy machine of FIG. 2 in accordance with the present invention.

In accordance with the present invention, data is stored in the treatment planning system 136 that allows a proper dose of electron radiation to be calculated that takes into account bremsstrahlung interactions as explained previously. The stored data is determined by following the correction process shown in FIG. 4. The correction process 200 is performed prior to applying electron radiation to a patient and may be performed at the manufacturer's premises or the therapy institution. The correction process 200 involves first retracting the leaves of the multileaf photon collimator 116b per step 202 so that the electron radiation beam is solely formed by the multileaf electron collimator 118.

The retraction for each leaf is dependent on a number of factors, such as beam energy, field size and the position of the leaves within the field. As an approximation, the retraction for each leaf of the collimator 116a is the same. At this stage, the penumbra and the electron output factor are ideal but the leakage outside the electron radiation field is not. The penumbra and electron output factor, $M_i$, are measured by a detector 138 per step 204. The penumbra may be defined as the perpendicular distance between the 50% and 80% isodose lines. In addition, the output factor is measured by "counting" the number of photons or electrons (or measuring the dose they deposit) crossing a plane at the isocenter. Signals representative of the detected penumbra and electron output factor, $M_i$, are sent to the computer 140.

Next, the computer 140 sends the representative control signals to the drive 122 via dose control unit 108 that causes each leaf of the multileaf photon collimator 116b to be moved into the electron radiation field by one unit per step 206. Once the leaves have been moved, the penumbra and output of the electron radiation field are measured per step 204 by the detector 138 as schematically shown in FIG. 5. In step 208, the penumbra $M_i$ measured in step 204 is compared with the penumbra $M_{i-1}$ previously measured in step 204 by the computer 140 by calculating the ratio $M_i/Mi_{-1}$. When the electron radiation field is perturbed enough that the penumbra measured in step 204 is significantly degraded, such as at least 2 millimeters or 5% or more of $M_{i-1}$, when compared with the penumbra $M_{i-1}$ previously measured in step 204, the computer 140 sends control signals to the drive 122 via dose control unit 108 that causes the leaves of the multileaf photon collimator to retract per step 210. The leaves may retract by an amount that may range from 1–2 centimeters. The exact amount is dependent upon electron energy and field size and shape.

The amount of retraction needed depends on the degree of lateral scatter of the electrons in the electron radiation beam. The amount of retraction may be experimentally derived from a number of factors as mentioned previously. However, since the predominant factor affecting the amount of retraction is the energy spectrum of the secondary electrons, that factor alone (calculated by physics theories or mathematical modeling known to one of ordinary skill in the art) can be used to determine the amount of retraction. The electron output factor with the leaves of the multileaf photon collimator in this configuration is noted and stored in a table 142 stored in computer 140. The table 142 stores the configuration of the photon collimator 116b that will reduce leakage and penumbra while maintaining an adequate electron output factor. The table 142 is accessible to the treatment planning computation programs used by the treatment planning system 136 so that the proper dose can be calculated.

The table 142 will need to be multi-dimensional because the degree of lateral scatter of the electrons is known to vary with both the energy of the beam and the field size. An individual electron field may have a complex shape (although most do not) and may be approximated by an equivalent field size in the table 142.

After the configuration of the photon collimator is determined per step 200, the photon collimator 116b is retained or moved to the determined configuration. A patient is placed in proper position via computer 140, gantry control 144 and table control 146 that controls table 146 in a manner similar to that described in U.S. patent application Ser. No. 09/910,526, filed on Jul. 20, 2001. After the patient is properly positioned, the electron and photon collimators are positioned based on the correction for bremsstrahlung interactions and the electron radiation beam is applied to the treatment area to generate a desired dosage. The computer 140 is operatively coupled to the dose control unit 108 which includes a dosimetry controller which is designed to control the beam source 106 to generate a desired beam achieving desired isodose curves.

Those skilled in the art will appreciate that various adaptations and modifications of the just described preferred embodiments can be configured without departing from the scope and spirit of the invention. Therefore, it is to be understood that, within the scope of the appended claims, the invention may be practiced other than as specifically described herein.

I claim:

1. A radiation therapy device, comprising:
   a radiation source that directs a beam along a beam path toward a treatment area;
   a beam shaping device controllable to selectively collimate said beam;
   a treatment planning system connected to said beam shaping device for simulating a beam shape delivered to a treatment zone, said treatment planning system comprising:
      a memory that stores treatment data; and
      a correction device that receives said data from said memory and calculates a proper dose that takes into account bremsstrahlung interactions caused by said beam interacting with said beam shaping device, said correction device controls said beam shaping device based on said calculated proper dose.

2. The radiation therapy device of claim 1, further comprising a gantry that rotates about an axis of rotation, said gantry containing said radiation source.

3. The radiation therapy device of claim 1, wherein said radiation source comprises an electron radiation source.

4. The radiation therapy device of claim 3, further comprising a photon radiation source.

5. The radiation therapy device of claim 3, wherein said radiation source comprises a linear accelerator.

6. The radiation therapy device of claim 1, wherein said beam shaping device comprises:
   a first collimator controllable to selectively collimate said beam; and
   a second collimator controllable to selectively collimate said beam.

7. The radiation therapy device of claim 6, further comprising:
   a first collimator drive operable to selectively position individual leaves of said first collimator; and
   a second collimator drive operable to selectively position individual leaves of said second collimator.

8. The radiation therapy device of claim 7, further comprising a control unit coupled to said radiation source and to said first and said second collimator drives to selectively deliver said calculated prescribed dose of radiation to a treatment area.

9. The radiation therapy device of claim 8, wherein said control unit is operable to control said radiation source to generate an electron beam and to cause said first collimator drive to position leaves of said first collimator to deliver said prescribed dose of radiation to said treatment area.

10. The radiation therapy device of claim 1, wherein said correction device optimizes a penumbra and electron output factor of said beam.

11. The radiation therapy device of claim 10, wherein said correction device determines a secondary electron range from mathematically modeling the energy spectrum of the secondary electrons scattered off said beam shaping device and said correction device retracts said beam shaping device by an amount based on said secondary electron range.

12. The radiation therapy device of claim 11, wherein said correction device compares said penumbra with a second penumbra measured by said correction device.

13. The radiation therapy device of claim 12, wherein said correction device retracts said beam shaping device by a predetermined amount if said comparing determines that said second penumbra differs from said penumbra by at least 5%.

14. A radiation therapy method, comprising:
    directing a beam along a beam path toward a treatment area;
    performing a correction process on said beam, said correction process comprising:
        selectively collimating said beam via a beam shaping device based on a dose that takes into account bremsstrahlung interactions caused by said beam interacting with said beam shaping device.

15. The method of claim 14, wherein said beam comprises electron radiation.

16. The method of claim 14, wherein said correction process comprises:
    retracting a first collimator so that said beam is totally formed by a second collimator.

17. A radiation therapy method, comprising:
    directing a beam along a beam path toward a treatment area;
    performing a correction process on said beam, said correction process comprising:
        selectively collimating said beam based on a dose that takes into account bremsstrahlung interactions caused by said beam;
        retracting a first collimator so that said beam is totally formed by a second collimator; and
        optimization of a penumbra and electron output factor of said beam.

18. The method of claim 17, wherein said correction process further comprises:
    determining a secondary electron range from mathematically modeling the energy spectrum of the secondary electrons scattered off the first collimator; and
    retracting said first collimator by an amount based on said secondary electron range.

19. The method of claim 17, wherein said correction process comprises moving said first collimator in a step wise manner into said beam.

20. The method of claim 19, wherein said correction process comprising measuring a second penumbra and a second electron output factor of said beam after said moving said first collimator is completed.

21. The method of claim 20, wherein said correction process further comprises:
    comparing said second penumbra with said penumbra;
    retracting said first collimator by a predetermined amount if said comparing determines that said second penumbra differs from said penumbra by at least 5%.

22. The method of claim 21, wherein said predetermined amount ranges from 1–2 centimeters.

23. The method of claim 20, wherein said correction process further comprises:
    comparing said second penumbra with said penumbra;
    moving said first collimator in a step wise manner into said beam if said comparing determines that said second penumbra differs from said penumbra by at least 5%.

24. A radiation therapy method, comprising:
    directing a beam along a beam path toward a treatment area;
    performing a correction process on said beam, said correction process comprising:
        selectively collimating said beam via a beam shaping device based on a dose that takes into account bremsstrahlung interactions caused by said beam interacting with said beam shaping device; and
        optimization of a penumbra and electron output factor of said beam.

25. The method of claim 24, wherein said beam comprises electron radiation.

26. The method of claim 24, wherein said correction process further comprises:
    determining a secondary electron range from mathematically modeling the energy spectrum of the secondary electrons scattered off the first collimator; and
    retracting said first collimator by an amount based on said secondary electron range.

27. The method of claim 24, wherein said correction process comprising measuring a second penumbra and a second electron output factor of said beam after said moving said first collimator is completed.

28. The method of claim 27, wherein said correction process further comprises:
    comparing said second penumbra with said penumbra;
    retracting said first collimator by a predetermined amount if said comparing determines that said second penumbra differs from said penumbra by at least 5%.

29. The method of claim 28, wherein said predetermined amount ranges from 1–2 centimeters.

30. The method of claim 27, wherein said correction process further comprises:
    comparing said second penumbra with said penumbra;
    moving said first collimator in a step wise manner into said beam if said comparing determines that said second penumbra differs from said penumbra by at least 5%.

* * * * *